USOO5605893A

United States Patent [19]
Kaufman

[11] Patent Number: 5,605,893
[45] Date of Patent: Feb. 25, 1997

[54] METHOD OF USING A THERAPEUTIC FOOD COMPOSITION TO DIMINISH BLOOD SUGAR FLUCTUATIONS IN DIABETIC PATIENTS

[75] Inventor: Francine Kaufman, Los Angeles, Calif.

[73] Assignee: Children's Hospital of Los Angeles, Los Angeles, Calif.

[21] Appl. No.: 418,210

[22] Filed: Apr. 7, 1995

Related U.S. Application Data

[63] Continuation-in-part of Ser. No. 213,542, Mar. 15, 1994, abandoned.

[51] Int. Cl.$^6$ .................................................. A61K 31/715
[52] U.S. Cl. ........................ 514/60; 424/439; 424/441; 426/808; 514/54; 514/866
[58] Field of Search ........................ 426/808; 514/54, 514/60, 866; 424/439, 441

[56] References Cited

U.S. PATENT DOCUMENTS

| | | | |
|---|---|---|---|
| 3,619,209 | 11/1971 | Hegadorn et al. | 426/103 |
| 3,969,514 | 7/1976 | Tiemstra | 426/573 |
| 4,629,725 | 12/1986 | Hiji | 514/53 |
| 5,097,023 | 3/1992 | Ducep et al. | 536/17.4 |
| 5,169,662 | 12/1992 | Spicer | 426/449 |
| 5,356,879 | 10/1994 | Zehner et al. | 514/23 |

FOREIGN PATENT DOCUMENTS

| | | |
|---|---|---|
| 0443789A1 | 8/1991 | European Pat. Off. . |
| 0504055A1 | 9/1992 | European Pat. Off. . |

OTHER PUBLICATIONS

L. Y. Dawson, *Clin. Diabetes*, 11(4):88–96 (1993).
J. I. Wolfsdorf et al., *Am. J. Clin. Nutrit.*, 52:1051–1057 (1990).
M. T. C. Ververs et al., *Eur. J. Clin. Nutrit.*, 47:268–273 (1993).
Ogata, et al., *Acta Paediatrica Japonica*, vol. 30, No. 5, pp. 547–552 (1988).
Boneh, et al., *Am. J. Clin. Nutr.*, vol. 47, No. 6, pp. 1001–1003 (1988).
Smit, et al., *Pediatric Research*, vol. 18, No. 9, pp. 879–881 (1984).
Chen, et al., *New England J. Medicine*, vol. 310, No. 3, pp. 171–174 (1984).
Behall, et al., *Am. J. Clin. Nutr.*, vol. 47, pp. 428–432 (1988).
Hengesh, *Princ. Medicinal Chemistry*, (W. Foye 3rd ed.), pp. 531–550, (1989).
Wolfsdorf, et al., *Am. J. Clin. Nutr.*, vol. 52, pp. 1051–1057 (1990).
Lozano et al., *Am. J. Clin. Nutr.*, vol. 52, pp. 667–670 (1990).
Ververs, et al., *European J. Clin. Nutr.*, vol. 47, No. 4, pp. 268–273 (1993).
Glaser, et al., *J. Pediatrics*, vol. 123, No. 4, pp. 644–650 (1993).
Weisenfeld, et al., *Proc. Soc. Exp. Biol & Med.*, vol. 202, No. 3, pp. 338–344 (1993).
Murphy, *The Magazine of Children's Hospital of Los Angeles*, Winter 1994/95, pp. 5–7.
PCT International Search Report of Corresponding to PCT Ser. No. PCT/US95/03330 (1995).
Kaufman, et al., *J. Inv. Med.*, vol. 43, Supp. 1, p. 188A (1995).
Wolfsdorf, et al., *Am. J. Clin. Nutr.*, vol. 56, pp. 587–592.
Simpson, et al., *Am. J. Clin. Nutr.*, vol. 42, pp. 462–469 (1985).

*Primary Examiner*—Gary L. Kunz
*Assistant Examiner*—Kathleen Kahler Fonda
*Attorney, Agent, or Firm*—Kirschstein, Ottinger, Israel & Schiffmiller, P.C.

[57] ABSTRACT

A therapeutic food composition for treatment of diabetic patients to diminish fluctuations in blood sugar levels and prevent hypoglycemic episodes, comprising per unit about 20–50 grams of nutrients including a slowly absorbed or digested complex carbohydrate, preferably cornstarch; a more rapidly absorbed complex carbohydrate; protein; and fat, but substantially no simple sugars. Diabetic patients may be treated to diminish blood sugar fluctuations and prevent hypoglycemia via the administration of the novel food composition as an evening or pre-bedtime snack or during the daytime hours to patients receiving insulin therapy or engaging in activities that might provoke hypoglycemia.

14 Claims, No Drawings

METHOD OF USING A THERAPEUTIC FOOD COMPOSITION TO DIMINISH BLOOD SUGAR FLUCTUATIONS IN DIABETIC PATIENTS

CROSS-REFERENCE TO RELATED APPLICATION

This application is a continuation-in-part of application Ser. No. 08/213,542, filed Mar. 15, 1994, now abandoned.

BACKGROUND OF THE INVENTION

1. Field of the Invention

This invention relates to therapeutic treatments of diabetes mellitus. More particularly, this invention relates to treatment methods and compositions for the prevention of severe fluctuations in blood sugar levels in diabetic patients.

2. Description of the Prior Art

Symptoms of hypoglycemia fall into two main categories. Rapid epinephrine release causes sweating, tremor, tachycardia, anxiety, and hunger. Central nervous system symptoms include dizziness, headache, clouding of vision, blunted mental acuity, confusion, abnormal behavior, convulsions and loss of consciousness. When hypoglycemia is recurrent or severe, nervous system symptoms predominate, and the epinephrine phase may not be recognizable. With more rapid drops or wide swings in plasma glucose (as in insulin reactions), adrenergic symptoms are prominent (*Harrison's Principles of Internal Medicine*, 11th Ed., McGraw-Hill Book Company, New York, 1987, p. 1800).

Numerous strategies have been developed to achieve the goal of maintaining blood glucose at a relatively constant level in diabetic patients, such as open looped continuous subcutaneous insulin pumps and multiple daily injections of insulin. These intensive insulin regimens are coupled with home glucose monitoring, and many patients measure their blood glucose levels by finger prick up to 6 to 8 times per day to assure that close to normal blood sugar levels are maintained. This regimen is prescribed because studies have shown that by avoiding excessive high blood sugar levels, the long-term outcome of patients with diabetes can be improved. However, this regimen, which decreases episodes of high blood sugar, also causes patients to experience more low blood sugar reactions (hypoglycemia).

Results of the Diabetes Complication and Control Trial indicate that intensive insulin treatment, while it markedly delays and lessens long term retinal, nephrologic and neuropathic disease, leads to a three to nine-fold increase in hypoglycemic events, most of which occur at night (L. Y. Dawson, *Clinical Diabetes*, 11:88–96, 1993). Sometimes these episodes of hypoglycemia are severe and can lead to loss of consciousness and convulsions. Severe hypoglycemic events seem to occur more often at night while the patient is asleep rather than during the day. When awake, diabetic patients can feel hypoglycemic reactions beginning, and can treat themselves with sugar in order to bring their blood sugar levels back into the normal range. When asleep, patients do not have this awareness, therefore the risk of hypoglycemia is much higher during this time.

The need exists to develop strategies to diminish hypoglycemia while continuing to intensively manage diabetes. Cornstarch has been used effectively to combat the hypoglycemia associated with glycogen storage disease type 1, a disease having an inherited absence or deficiency of glucose-6-phosphatase activity in the liver, kidneys, and intestines, leading to accumulation of glycogen in those organs and hypoglycemia during fasting. Protection against low blood sugar was provided for up to 6 to 8 hours after ingestion of uncooked cornstarch (J. I. Wolfsdorf, et al., *Am. J. Clin. Nutr.*, 51:1051–7, 1990). However, the dosage of cornstarch used for this treatment was 1.75 grams per kilogram of body weight. This dosage is much higher than could be tolerated by a patient with diabetes mellitus.

Another study has also been conducted in patients with diabetes, giving cornstarch during inpatient hospitalization, with a reduction in the nadir of the blood glucose level. Children were fasted and then given the entire carbohydrate content of the standard bedtime snack (30 grams of carbohydrate) as uncooked cornstarch (M. T. Ververs, et al., *Eur. J. Clin. Nutr.*, 47:268–73, 1983). However, in this study the cornstarch did little to prevent hypoglycemia and the researchers did not evaluate varying dosages to determine maximal efficacy.

Thus, the need exists for a better method of treating hypoglycemia in both Type I and Type II diabetics. In particular, a method of treatment or maintenance is required which will avoid serious hypoglycemic episodes while not provoking hyperglycemia.

SUMMARY OF THE INVENTION

Blood glucose levels in patients with diabetes mellitus are regulated and stabilized by ingesting a therapeutic food composition including a slowly metabolized complex carbohydrate, preferably uncooked cornstarch, a more rapidly metabolized complex carbohydrate, protein and fat. The food composition is slowly absorbed from the gastrointestinal tract and maintains relatively stable blood sugar levels in the diabetic patient for up to nine hours.

The food composition, which may be in the form of a snack bar, is preferably administered to diabetic patients shortly before bedtime, and is effective in substantially preventing nocturnal episodes of hypoglycemia while not causing hyperglycemia.

DETAILED DESCRIPTION OF THE INVENTION

The present invention pertains to a therapeutic food composition intended for administration to patients suffering from Type I or Type II diabetes to help maintain proper blood glucose regulation and prevent wide fluctuations therein, namely, hypoglycemic and hyperglycemic episodes. The therapeutic composition is to be administered as part of an overall program of treatment, including control of diet and the administration of insulin and/or other medications in appropriate cases.

The novel food composition comprises as its essential components:

a) a complex carbohydrate which is slowly absorbed from the human gastrointestinal tract (hereinafter "slowly absorbed carbohydrate"), i.e., is slowly digested and is not completely metabolized even after 3–4 hours;

b) a complex carbohydrate which is more rapidly absorbed from the digestive tract (hereinafter "rapidly absorbed carbohydrate");

c) protein; and d) fat.

As used herein, the term "complex carbohydrates" refers to macromolecular carbohydrates including starches, polydextrose and other polysaccharides.

The therapeutic composition containing the foregoing components may be in any conventional "snack" form, e.g., bars, puddings, cookies, wafers, milkshakes and the like. Snack-type bars resembling candy or granola bars are most convenient for storage, handling and administration purposes and, when produced with scores, perforations or grooves thereon, can be easily divided for purposes of administering a fraction of a bar where appropriate.

The novel food composition preferably contains about 20 to about 50 grams of nutrients per serving or unit, e.g., per bar, including:

about 17–24 grams of total carbohydrates (about 5–15 grams of slowly absorbed carbohydrate and about 7–19 grams of rapidly absorbed carbohydrate);

about 5–20 grams of protein; and about 3–7 grams of fat, preferably at least one-third monounsaturated fat.

The term "nutrients" as used herein refers to carbohydrates, proteins and fats.

The therapeutic food compositions of the invention preferably provides about 115–230 calories per serving or unit, of which:

about 50–70% are from slowly absorbed and rapidly absorbed complex carbohydrates;

about 15–25% are from protein; and about 15–25% are from fat.

In a preferred embodiment of the invention, the novel food composition is in the form of a bar including 17–24 grams of total carbohydrate, or the equivalent of one to one and one-half "bread exchanges" in a standard diabetic diet plan. The bar contains about 5–15 grams of slowly absorbed carbohydrate in the form of uncooked cornstarch, which generally comprises by weight about 27% amylose and 73% amylopectin. The preferred embodiment also contains about 7–19 grams of rapidly absorbed complex carbohydrate, but substantially no simple sugars; about 5–20 grams of protein; and about 3–7 grams of fat, at least one-third as monounsaturated fat.

The ingredients in the therapeutic food composition may include any conventional food ingredients of adequate purity and wholesomeness which preferably supply the aforementioned amounts of total calories and percentage of calories from carbohydrates, protein and fat, respectively, and wherein the relative weight ranges of slowly absorbed carbohydrates, rapidly absorbed carbohydrates, protein and fat are as indicated previously. In the preferred embodiment of a snack-type bar, the ingredients may include, by way of illustration, uncooked cornstarch as the slowly absorbed carbohydrate; polydextrose, peanuts, peanut derivatives (e.g., peanut butter), other nuts or nut derivatives as sources of rapidly absorbed carbohydrates, fat and protein; and other protein sources such as soy protein, whey protein, and casein hydrolysate. Artificial sweeteners or sugar substitutes (e.g., aspartame or sorbitol) may be included in the food composition, but no simple sugars such as sucrose. Coloring agents, water, salt, preservatives and other standard ingredients or additives normally used in the preparation of a snack or candy-type bar may be utilized as well, provided that the total nutrient and calorie profile of the finished bar or other form of the novel food composition comes within the parameters defined above.

Uncooked cornstarch is the preferred source of slowly absorbed carbohydrate for purposes of the invention since its carbohydrate content and its rate of metabolism are known and are relatively uniform, and it may be readily formulated into a variety of palatable food compositions.

Many diabetics routinely consume a bedtime snack containing about 30 grams of carbohydrate, often in the form of bread, cereal or milk. By the method of treatment of the present invention, patients suffering from diabetes mellitus are administered in place of, or as part of, their normal evening or pre-bedtime snack (in accordance with their recommended bread and protein exchanges) one to two servings or units of the therapeutic food composition, for example one to two bars prepared in accordance with the invention. The number of units administered, including fractions of a unit (such as half bars), will depend on the age, weight and condition of the patient, whether or not the patient takes insulin or other antidiabetic medication and the patient's nocturnal blood sugar profile as determined by finger stick blood glucose levels or other means of blood sugar management. The goal of the treatment is to prevent blood glucose levels from dropping below 60 mg/dl, defined as hypoglycemia, while not rising above 250 mg/dl, defined as hyperglycemia.

Dosage amounts of less than one unit may be utilized in younger pediatric patients or in patients who have demonstrated relatively little tendency towards nocturnal hypoglycemic events.

It has been found in clinical studies with diabetic children and adolescents that food compositions prepared in accordance with the invention and administered as described herein are effective in maintaining blood sugar levels in the "normal" range of 60 mg/dl–250 mg/dl for as long as 8–9 hours or more after ingestion.

Patients taking insulin to facilitate post-prandial absorption of glucose can also be treated during the day with premeasured doses of the novel food composition, which will be slowly metabolized to the monosaccharide glucose over a period of six to eight hours, instead of receiving simple carbohydrates such as orange juice or other sugar sources that tend to cause a rapid peak in blood glucose level that quickly subsides. During waking hours the patient's use of, and hence requirement for, glucose is varied and depends upon the level and type of activity, e.g., vigorous exercise. The exact amount and frequency of the actual dose, therefore, will vary by patient and from day to day for each patient. A blood glucose test, usually administered as a finger stick to obtain a blood sample, can be used to monitor daily glucose levels as well as the patient's own subjective experience of symptoms associated with the onset of hypoglycemia. Therefore, in the practice of this invention sufficient complex carbohydrate is administered in the form of the novel food composition to maintain the blood glucose level somewhat above this level, nominally about 60 mg/dl in the average patient.

It will be appreciated by persons of skill in the medical arts generally and in the management of diabetic patients specifically that the composition and method of the present invention are valuable adjuncts to conventional diet management and drug or insulin therapy and can provide an easily administered and accepted modality to avoid excessive peaks and valleys in blood glucose levels, particularly the severe hypoglycemic episodes which are experienced by many diabetics.

The following are illustrative examples of the novel composition and method of the present invention. These examples are not intended, however, to provide ingredients, specific formulations, methods of production or dosage regimens which must be utilized exclusively to practice the present invention.

EXAMPLE 1

Cornstarch-containing Bar

A therapeutic food composition was prepared in accordance with the invention in the form of a snack-type vanilla nut bar. The bar weighed a total of 31 g and contained sorbitol, cornstarch, soy protein isolate, peanut butter, water, polydextrose, peanuts, whey protein concentrate, natural flavors, lecithin and citric acid.

Nutritionally, the bar provided 120 calories (equivalent to one bread exchange), of which about 54% were from carbohydrates, 23% from protein and 23% from fat. The bar included 7 g of protein and about 3 g of total fat: about 0.5 g saturated fat, 1 g polyunsaturated fat and 1 g monounsaturated fat.

The total carbohydrate content of the bar was 17 g, of which 5 g were cornstarch (uncooked) and about 12 g were more rapidly absorbed carbohydrate provided primarily by the polydextrose and peanuts.

The bar contained 95 mg of sodium and 40 mg of potassium.

EXAMPLE 2

Treatment of Diabetic Patients

The bar of Example 1 was administered to eight diabetic children who had previously experienced episodes of nocturnal hypoglycemia. Each child consumed one bar as part of his or her regular evening snack for three to five consecutive nights, and the blood glucose levels of each patient were measured several times during the night and in the morning upon awakening.

As indicated by the data set forth in Table 1, only one patient exhibited hypoglycemia after consuming the therapeutic bar and only in one blood sugar reading out of well over a dozen taken from that patient, with hypoglycemia being defined as blood glucose levels <60 mg/dl. By contrast, the patients had all previously experienced moderate to severe episodes of nocturnal hypoglycemia after consuming their regular evening snacks which did not contain cornstarch.

TABLE 1

| | Blood Glucose Readings (mg/dl) | | | | |
|---|---|---|---|---|---|
| Day | 1 | 2 | 3 | 4 | 5 |
| | Patient 1: | | | | |
| 0 | 68 | 340 | 188 | 221 | 172 |
| 1 | 65 | | | | |
| 2 | 103 | 248 | 197 | 161 | 169 |
| 3 | 86 | | | | |
| 4 | 116 | | | | |
| 5 | 165 | 203 | 169 | 149 | 139 |
| 6 | 175 | | | | |
| 7 | 204 | | | | |
| 8 | 236 | 177 | 141 | 115 | 81 |
| | Patient 2: | | | | |
| 0 | 57 | 74 | 61 | 165 | |
| 1 | | 77 | | | |
| 2 | | 64 | | | |
| 3 | 86 | 82 | 72 | 78 | |
| 4 | | 81 | | | |
| 5 | | 77 | | | |
| 6 | | 96 | 94 | 182 | 125 |
| 7 | | 98 | | | |
| 8 | 80 | 82 | 172 | 163 | |
| | Patient 3: | | | | |
| 0 | 144 | 51 | 219 | 256 | 101 |
| 1 | 201 | | | | |
| 2 | 146 | 226 | 153 | 106 | 88 |
| 3 | 176 | | | | |
| 4 | 96 | 101 | 180 | 87 | 93 |
| 5 | 74 | | | | |
| 6 | 98 | 131 | 155 | 86 | 85 |
| 7 | 92 | | | | |
| 8 | 114 | 211 | 279 | 114 | 142 |
| | Patient 4: | | | | |
| 0 | 160 | 144 | 88 | 96 | 144 |
| 1 | 102 | | | | |
| 2 | 100 | 95 | 66 | 206 | 228 |
| 3 | | | | | |
| 4 | 97 | 50 | 83 | 265 | 146 |
| 5 | | | | | |
| 6 | 105 | | | | |
| 7 | | | | | |
| 8 | 122 | 153 | 72 | 203 | 84 |
| | Patient 5: | | | | |
| 0 | 53 | 154 | 99 | 117 | 68 |
| 1 | 164 | 122 | 138 | 199 | 85 |
| 2 | 128 | 157 | 148 | 194 | 103 |
| 3 | 146 | 158 | 175 | 175 | 86 |
| 4 | 124 | 156 | 122 | 124 | 116 |
| 5 | 116 | 157 | 131 | 140 | 165 |
| 6 | 102 | 156 | 105 | 139 | 175 |
| 7 | 108 | 160 | 107 | 132 | 204 |
| 8 | 118 | 167 | 110 | 149 | 285 |
| | Patient 6: | | | | |
| 0 | 52 | 129 | 212 | | |
| 1 | | | | | |
| 2 | | | | | |
| 3 | 106 | 83 | 188 | | |
| 4 | | | | | |
| 5 | | | | | |
| 6 | 97 | 132 | | | |
| 7 | | | | | |
| 8 | 124 | 175 | 179 | | |
| | Patient 7: | | | | |
| 0 | 134 | 78 | 67 | 242 | |
| 1 | | | | | |
| 2 | | | | | |
| 3 | | | | | |
| 4 | | | | | |
| 5 | | | | | |
| 6 | 177 | 115 | 132 | | |
| 7 | | | | | |
| 8 | 196 | 132 | 169 | 205 | |
| | Patient 8: | | | | |
| 0 | 320 | 160 | 365 | | |
| 1 | | | | | |
| 2 | 269 | 327 | 264 | | |
| 3 | | | | | |
| 4 | | | | | |
| 5 | | | | | |
| 6 | 282 | 387 | 228 | | |
| 7 | | | | | |
| 8 | 175 | 322 | 223 | | |

The unique formulation of the novel food composition, blending slowly and rapidly absorbed carbohydrates, protein and fat, allows for the gradual hydrolysis and absorption of the complex carbohydrates and maintains the blood sugar level stable for up to eight to nine hours, diminishing hypoglycemia in diabetic subjects after the post-prandial period.

It has thus been shown that there are provided compositions and methods which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the following claims:

1. A method of treating a diabetic patient to diminish fluctuations in blood sugar levels and prevent hypoglycemic episodes, said method consisting of the administration to the patient of a therapeutic food composition comprising per serving or unit about 20–50 grams of nutrients including:

a) about 5–15 g of slowly absorbed complex carbohydrate;

b) about 7–19 g of rapidly absorbed complex carbohydrate;

c) about 5–20 g of protein; and d) about 3–7 g of fat, said composition being substantially free of simple sugars.

2. A method according to claim 1 wherein said composition comprises per unit about 17–24 g of total carbohydrates.

3. A method according to claim 1 wherein said slowly absorbed carbohydrate is cornstarch.

4. A method according to claim 3 wherein said cornstarch is uncooked.

5. A method according to claim 3 wherein said composition comprises about 5 g of cornstarch per unit.

6. A method according to claim 1 wherein at least one-third of said fat is monounsaturated.

7. A method according to claim 1 wherein said composition is in the form of a snack bar, pudding, cookie, wafer or milkshake.

8. A method according to claim 7 wherein said composition is in the form of a snack bar.

9. A method according to claim 8 wherein said bar is produced with scores, perforations or grooves thereon for easy division into fractions of a unit.

10. A method according to claim 1 wherein about 1–2 units of said composition are administered to the patient.

11. A method according to claim 1 wherein one half unit of said composition is administered to the patient.

12. A method according to claim 1 wherein said composition is administered to the patient as an evening or pre-bedtime snack.

13. A method according to claim 1 wherein said composition is administered during the daytime to a patient receiving insulin therapy or engaging in exercise.

14. A method according to claim 1 wherein said patient is a child or adolescent.

* * * * *